United States Patent
Hall et al.

(10) Patent No.: US 6,653,499 B1
(45) Date of Patent: Nov. 25, 2003

(54) PHOTOACTIVE PROPANE DERIVATIVES AND ORIENTATION LAYERS

(75) Inventors: Alan W Hall, Hull (GB); Stephen M Kelly, Hull (GB); Gareth J Owen, Hull (GB); Ridvan Karapinar, Van (TR); Mary O'Neill, Hull (GB)

(73) Assignee: Qinetiq Limited, London (GB)

( * ) Notice: Subject to any disclaimer, the term of this patent is extended or adjusted under 35 U.S.C. 154(b) by 0 days.

(21) Appl. No.: 09/857,621

(22) PCT Filed: Dec. 16, 1999

(86) PCT No.: PCT/GB99/04287

§ 371 (c)(1),
(2), (4) Date: Jun. 7, 2001

(87) PCT Pub. No.: WO00/37453

PCT Pub. Date: Jun. 29, 2000

(30) Foreign Application Priority Data

Dec. 22, 1998 (GB) ............................................. 9828124

(51) Int. Cl.$^7$ ............................................. C07C 69/00
(52) U.S. Cl. ........................... 558/414; 560/59; 560/61; 428/1.26; 252/299.62
(58) Field of Search ............................ 558/414; 560/59, 560/61; 428/1.26; 252/299.62

(56) References Cited

FOREIGN PATENT DOCUMENTS

| EP | 0 611 786 | 8/1994 |
| EP | 0 700 981 | 3/1996 |
| WO | WO96/10049 | 4/1996 |

OTHER PUBLICATIONS

Chemical Abstracts, vol. 116, No. 20, May 1992, Columbus, Ohio, US; abstract No. 204352, Xu, Yaokun et al.: "Photoresist composition containing photosensitive acrylic resin" abstract & CN 1 040 602 (WUXI Chemical Research and Design Institute, Peop. Rep. China) Mar. 1990.

Awl, R. A. et al.: "Cyclic fatty esters: synthesis, characterization, and lipolysis of isomeric triglycerides of 9–(6–propyl–3–cyclohexenyl)–(Z)–8–nonenoic acid" Chem. Phys. Lipids (1986), 41(1), 65–80, 1986.

Shukla, Vijai K. S. et al.: "High–performance liquid chromatography of triglycerides of Flacourtiacease seed oils containing cyclopentenyl fatty acids (chaulmoogrid oils)" J. Chromatogr. (1985), 348(2), 441–6, 1985.

*Primary Examiner*—Richard L. Raymond
(74) *Attorney, Agent, or Firm*—Nixon & Vanderhye P.C.

(57) ABSTRACT

Compounds of formula (I) may be used as alignment layers in liquid crystal devices wherein $X_{1-5}$ are idependently selected from H, F, CN, phenylene, $C_{1-10}$ alkyl, whereby when $X_1=X_2$, then $X_{1,2}=H$ and when $X_3=X_4$, then $X_{3,4}=H$, $S_{1-3}$ are spacer units, $PG_{1-3}$ are photoisomerisable/dimerisable groups.

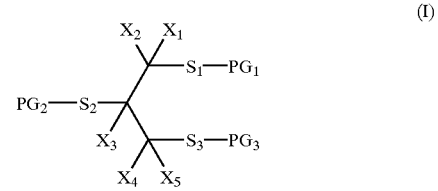

12 Claims, 2 Drawing Sheets

PHOTOACTIVE PROPANE DERIVATIVES AND ORIENTATION LAYERS

This application is a 371 of PCT/GB99/04287, filed Dec. 16, 1999.

The present invention describes materials and methods for achieving alignment of liquid crystal materials on a substrate surface and devices fabricated using these methods and materials.

Liquid crystal display devices (LCDs) or light shutters generally comprise a layer of liquid crystalline material between two solid substrates to form a cell. These substrates are generally coated with a conducting material, such as Indium/Tin Oxide (ITO) to form electrodes or electrode patterns. An electric field applied across the cell or between the electrodes switches the liquid crystal between different molecular arrangements or states. Thus the light transmission through the cell can be modulated depending on the cell configuration, the type of liquid crystalline material, the presence of polarisers, etc. A preferred molecular alignment direction and pretilt angle ($\theta$) is imparted by an alignment layer on top of the electrodes and in contact with the liquid crystalline material.

It is well known in the art that fabrication of liquid crystal devices which have advantageous performance and low defect densities requires control of the alignment of the liquid crystalline material at the surfaces of the device. Different types of liquid crystal alignment have been described. Homeotropic alignment refers to an alignment in which the unique optical axis of a liquid crystal phase is held perpendicular to the adjacent surface.

Planar alignment, sometimes referred to as homogeneous alignment, refers to alignment in which the unique optic axis of the liquid crystal phase lies parallel to the adjacent surface. Planar alignment may also impose a direction in which the optic axis of the liquid crystal lies in the plane of the adjacent surface.

Tilted planar alignment or tilted homogeneous alignment refer to alignment in which the liquid crystal unique optic axis lies at an angle, termed the pretilt angle ($\theta$) from the plane of the adjacent surface. The pretilt angle may be as small as a fraction of one degree or as large as several tens of degrees.

Tilted homeotropic alignment refers to an alignment in which the optic axis of the liquid crystal lies tilted away from the normal to the adjacent surface. This deviation is again termed a pretilt angle.

In liquid crystal devices, said alignment geometries are chosen and used in combination to achieve specific optical and electro-optic properties from the device and may be combined in new ways or with new liquid crystalline mixtures to provide new types of devices.

Several methods are known in the art by which defined liquid crystal alignment may be achieved. Deposition of a polymer layer, for example a polyimide layer, on the substrate surface followed by mechanical rubbing provides a pretilted planar alignment. A planar alignment or tilted planar alignment may also be achieved by evaporating a variety of inorganic substances, for example $SiO_x$, onto the surface from an oblique angle of incidence. A disadvantage of this method is that it requires slow and costly vacuum processing. A further disadvantage is that the resulting evaporated layer may show a high capacity to absorb contaminants onto itself from the environment or from other materials used in fabrication of the device.

A homeotropic alignment can be obtained by depositing a surfactant, for example a quaternary ammonium salt, onto the surface from solution in a suitable solvent, a disadvantage of this treatment is that the resistivity of the liquid crystal device may be lowered by the surfactant and the resulting alignment may also show poor stability.

Structured alignment patterns of subpixel size and above can be achieved by illumination of a polymer layer containing photochemically orientable dyes or photochemically dimerisable and/or isomerisable molecules, as described, for example, in EP-A-0445629. A disadvantage of this method is that the solubility of the dye molecules in the polymer matrix is limited and the chemical and photochemical stability over time is insufficient.

Another method for achieving structured non-contact orientation is the photodimerisation of polymers incorporating photodimerisable groups, such as cinnamate or coumarin derivatives, as described, for example, in Jpn. J. Appl. Phys., Vol., 31, 2155 (1995) and EP-A-9410699.0. A disadvantage of these materials is the polydispersity of the materials produced by polymerisation. This requires, for example, different solution concentrations for spin coating depending on the average molecular weights of the polymers which can not be determined with any great accuracy and which are often not reproducible from one batch to another. This can give rise to unreproducible alignment as well as also requiring repeated purification cycles of the polymer product in order to remove unreacted monomer and oligomers. The attachment of low molar mass photoreactive units to monodispersed polymer backbones can lead to polymers with unreacted sites, which can give rise to dielectric breakdown of cells containing such materials. This is especially important for active matrix devices.

An object of this invention is to provide means of achieving a defined surface alignment of a liquid crystalline material on a substrate surface, which does not require mechanical rubbing or other methods of physical contact which may damage the surface or structures on the surface. This is especially important for active matrix displays based on the use of surface mounted thin film transistors. Static electricity or dust caused by mechanical rubbing or buffing polymer layers, such as polyimide or polyamide, in order to induce a unidirectional alignment due to microgrooves can cause defects in thin film transistors and lead to dielectric breakdown. Such alignment layers also suffer from the disadvantage that the microgrooves possess inherent defects themselves, which can result in random phase distortion and light scattering. This impacts detrimentally on the optical appearance of the displays or the efficiency of the light shutters. Additionally, mechanical buffing does not allow locally oriented regions of the surface to be aligned with different azimuthal angles. This is a substantial drawback since sub-pixelisation can lead to higher contrast and an improved optical efficiency.

According to this invention compounds are provided of Formula I:

Formula I wherein
$X_{1-5}$ are independently selected from H, F, CN, phenylene, $C_{1-10}$ alkyl whereby when $X_1=X_2$, then $X_{1,2}$=H and when $X_3=X_4$, then $X_{3,4}$=H $S_{1-3}$ are spacer units $PG_{1-3}$ are photoisomerisable/dimerisable groups.

The term "spacer units" $S_{1-3}$ include, for example, independently of one another, an alkylene unit with 1 to 16, preferably 1 to 10, carbon atoms wherein the alkylene unit may have one or more non-adjacent $CH_2$ groups substituted with COO, OOC, O;

a cycloalkylene group with 3 to 8 carbon atoms, preferably with 5 or 6 carbon atoms, in which optionally one or two methylene units can be replaced by NH groups;

phenylene, which can be unsubstituted or substituted from one and up to and including all available substitution positions with $C_{1-10}$ alkyl, $C_{1-10}$ alkoxy, CN, $NO_2$, halogen, or carbonate;

COO, OOC;

an amide group, that is, —CONH— and —NHOC—, the H group on the amide may be substituted with $C_{1-10}$ alkyl groups;

an ether group, that is COC.

Particularly preferred spacer groups for $S_{1-3}$ include oxycarbonylalkanoyloxy, oxyalkoxy, oxycarbonylalkoxy, oxyalkanoyloxy, oxycarbonylphenoxyalkanoyloxy, oxyalkoxyalkyl containing from 1–16 carbon atoms.

The isomerisable/dimerisable units $PG_{1-3}$ are molecular units which can undergo either photochemical cis/trans isomerisation and/or photochemical cycloaddition and thus lead to a cross-linking of the molecule. The isomerisation/dimerisation units $PG_{1-3}$ are linked via the spacer units $S_{1-3}$ to the propane backbone and can either have the general formula II

II wherein

A may be 1,2-, 1,3- or 1,4-phenylene, which is unsubstituted or substituted from one and up to and including all available substitution positions with one or more of the groups selected from halogen, CN, $NO_2$ and in which 1 or 2 CH groups can be replaced by nitrogen, or A may be 2,5-thiophenediyl, 2,5-furanylene, 1,4- or 2,6-naphthalene in which 1 or 2 CH groups can be replaced by nitrogen;

$A_1$ may be 1,2-, 1,3- or 1,4-phenylene, which is unsubstituted or substituted from one and up to and including all available substitution positions with one or more of the groups selected from halogen, CN, $NO_2$ and in which 1 or 2 CH groups can be replaced by nitrogen, or $A_1$ may be 2,5-thiophenediyl, 2,5-furanylene, 1,4- or 2,6-naphthalene in which 1 or 2 CH groups can be replaced by nitrogen;

$A_{2,3}$ may each independently be selected from 1,2-, 1,3- or 1,4-phenylene, which is unsubstituted or substituted from one and up to and including all available substitution positions with one or more of the groups selected from halogen, CN, $NO_2$ and in which 1 or 2 CH groups can be replaced by nitrogen;

or $A_{2,3}$ may each independently be selected from 2,5-thiophenediyl, 2,5-furanytene, 1,4- or 2,6-naphthalene in which 1 or 2 CH groups can be replaced by nitrogen, trans-1,3-dioxane-2,5-diyl or 1,4-piperidyl;

$Z_{1,2}$ may each independently be selected from a direct bond, $CH_2CH_2$, COO, OOC, $O(CH_2)_3$, $OCH_2$, $CH_2O$, $(CH_2)_3O$, $(CH_2)_4$, or the trans form of $OCH_2CH=CH$, $CH_2CH=CHO$, $CH_2CH_2CH=CH$, $CH_2CH=CHCH_2$;

$n_{1,2}$ may each independently be 0 or 1;

W, Y may each independently be selected from H, halogen, CN, alkyl with 1 to 12 carbon atoms which is optionally substituted with one or more fluorines and in which optionally 1 or 2 non-adjacent methylene units ($CH_2$) can be replaced by oxygen, COO, OOC, CO and/or CH=CH, $R_1$ may be H, halogen, CN, $NO_2$, NCS, alkyl with 1 to 12 carbon atoms which is optionally substituted with one or more fluorines and in which optionally 1 or 2 non-adjacent methylene units ($CH_2$) can be replaced by oxygen, COO, OOC, CO and/or CH=CH;

or $PG_{1-3}$ may have the formula III

III wherein

$A_{4,5}$ may each independently be selected from 1,2-, 1,3- or 1,4-phenylene, which is unsubstituted or substituted from one and up to and including all available substitution positions with one or more of the groups selected from halogen, CN, $NO_2$ and in which 1 or 2 CH groups can be replaced by nitrogen;

or $A_{4,5}$ may be independently seiected from 2,5-thiophenediyl, 2,5-furanylene, 1,4- or 2,6-naphthalene in which 1 or 2 CH groups can be replaced by nitrogen;

$Z_{3,4}$ may each independently be selected from a direct bond, $CH_2CH_2$, COO, OOC, $O(CH_2)_3$, $OCH_2$, $CH_2O$, $(CH_2)_3O$, $(CH_2)_4$, or the trans form of $OCH_2CH=CH$, $CH_2CH=CHO$, $CH_2CH_2CH=CH$, $CH_2CH=CHCH_2$;

$n_{3,4}$ may each independently be 0 or 1;

$A_6$ may be

A₇ may be 1,2-, 1,3- or 1,4-phenylene, which is unsubstituted or substituted from one and up to and including all available substitution positions with one or more of the groups selected from halogen, CN, NO₂ and in which 1 or 2 CH groups can be replaced by nitrogen, or A₇ may be 2,5-thiophenediyl, 2,5-furanylene, 1,4- or 2,6-naphthalene in which 1 or 2 CH groups can be replaced by nitrogen, trans-1,3-dioxane-2,5-diyl or 1 4-piperidyl;

Z₅ may be an alkylene unit with 1 to 16, preferably 1 to 10, carbon atoms, a cycloalkylene group with 3 to 8 carbon atoms, preferably with 5 or 6 carbon atoms, in which optionally one or two methylene units can be replaced by NH groups, or phenylene, which can be substituted from one and up to and including all available substitution positions with one or more of the groups selected from $C_{1-10}$ alkyl, $C_{1-10}$ alkoxy, CN, NO₂, halogen, or carbonate, an ester group, that is, COO and OOC;
an amide group, that is, —CONH— and —NHOC—, the H group on the amide may be substituted with $C_{1-10}$ alkyl groups;
an ether group, that is, COC;
n₅ may be 0 or 1;
R₂ may be H, halogen, CN, NO₂, NCS, SCN, alkyl with 1 to 12 carbon atoms which is optionally substituted with one or more fluorines and in which optionally 1 or 2 non-adjacent methylene units (CH₂) can be replaced by oxygen, COO, OOC, CO and/or CH=CH;

R₃ may be H, halogen, CN, NO₂, NCS, SCN, alkyl with 1 to 12 carbon atoms which is optionally substituted with one or more fluorines and in which optionally 1 or 2 non-adjacent methylene units (CH₂) can be replaced by oxygen, COO, OOC, CO and/or CH=CH;

R₄ may be H or $C_{1-10}$ alkyl;

V may be H, alkyl or alkoxy with 1 to 8 carbon atoms, trifluoromethyl, or phenyl which may be substituted from one and up to and including all available substitution positions with one or more of the groups selected from CN, halogen, NO₂;

U may be H, alkyl or alkoxy with 1 to 8 carbon atoms, cyano, or COOR₅;

R₅ may be $C_{1-10}$ alkyl;

r may be a number from 0 to 3;

$X_{6,7}$ may be independently selected from H, halogen, CN, NO₂, NCS, SCN, alkyl with 1 to 12 carbon atoms which is optionally substituted with one or more fluorines and in which optionally 1 or 2 non-adjacent methylene units (CH₂) can be replaced by oxygen, COO, OOC, CO and/or CH=CH.

The term "1,2-, 1,3- or 1,4-phenylene, which is unsubstituted or substituted with one or more of the groups selected from halogen, CN and/or NO₂ and in which 1 or 2 CH groups can be replaced by nitrogen" includes, and is not limited to, in the present application 1,2-phenylene, 1,3-phenylene or 1,4-phenylene, 2-fluoro-1,4-phenylene, 2,3-difluoro-1,4-phenylene, 2,6-difluoro-1,4-phenylene, 2-chloro-1,4-phenylene, 2,3-dichloro-1,4-phenylene, 2,6-dichloro-1,4-phenylene, 2-cyano-1,4-phenylene, 2,3-dicyano-1,4-phenylene, 2-nitro-1,4-phenylene, 2,3-dinitro-1,4-phenylene, 2-bromo-1,4-phenylene, 2-methyl-1,4-phenylene, and pyridine-2,5-diyl, pyrimidine-2,5-diyl, and the like. Particular examples that are preferred include 1,4-phenylene, 2-fluoro-1,4-phenylene, 2,3-difluoro-1,4-phenylene, 2,6-difluoro-1,4-phenylene, pyridine-2,5-diyl, pyrimidine-2,5-diyl.

The term "1,4- or 2,6-naphthalene, in which 1 or 2 CH groups can be replaced by nitrogen" includes, and is not limited to, in the present application 1,4- or 2,6-naphthalene, 1-benzazine-2,6-diyl and 2-benzazine-1,4-diyl.

Examples of the term "alkyl with 1 to 12 carbon atoms which is optionally substituted with one or more fluorines and in which optionally 1 or 2 non-adjacent methylene units (CH₂) can be replaced by oxygen, COO, OOC, CO and/or CH=CH" include in the present application straight-chain and branched (optionally chiral) residues such as alkyl, alkenyl, alkoxy, alkenyloxy, alkoxyalkyl, alkoxyalkenyl, 1-fluoroalkyl, terminal trifluoromethylalkyl, terminal difluoromethylalkyl, terminal trifluoromethylalkoxy, and the like with 1 or, 2 to 16 carbon atoms. Examples of preferred residues are methyl, ethyl, propyl, butyl, pentyl, hexyl, heptyl, octyl, 1-methylpropyl, 1-methylheptyl, 2-methylbutyl, 3-methyl pentyl, vinyl, 1E-propenyl, 1E-butenyl, 1E-pentenyl, 3-butenyl, 3E-pentenyl, 3E-hexenyl, 3E-hexenyl, 4-pentenyl, 4Z-hexenyl, 5-hexenyl, 6-heptenyl, 7-octenyl, methoxy, ethoxy, propyloxy, butyloxy, pentyloxy, hexyloxy, octyloxy, 1-methylpropyloxy, 1-methylheptyloxy, 2-methylbutyloxy, 1-fluoropropyl, 2-fluoropropyl, 2,2-difluoropropyl, 3-fluoropropyl, 3,3-difluoropropyl, 3,3,3-trifluoropropyl and the like. Especially preferred residues possess 1 or, respectively, 2 to 6 carbon atoms.

The term "halogen" may represent in the present application fluorine, chlorine, bromine and iodine, but especially fluorine and chlorine.

The structural and other preferences are expressed below on the basis of inter alia one or more of the following properties—good processability, thermal, chemical and electrochemical stability, ability to isomerise and/or dimerise, monodispersity and ready synthesis from commercially available starting materials.

Overall preferred structures for the groups $PG_{1-3}$ are those listed below:

IIA wherein $S_1$ indicates the position of the spacer group $A_1$ may be 1,4-phenylene, which is unsubstituted or substituted with one or more of the groups selected from halogen, CN, $NO_2$;

or pyrimidine-2,5-diyl, pyridine-2,5-diyl, 2,5-thiophenediyl, 2,5-furanylene, 1,4- or 2,6-naphthalene;

$A_2$ may be 1,4-phenylene, which is unsubstituted or substituted from one and up to and including all available substitution positions with one or more of the groups selected from halogen, CN, $NO_2$;

or pyrimidine-2,5-diyl, pyridine-2,5-diyl, 2,5-thiophenediyl, 2,5-furanylene, trans-1,3-dioxane-2,5-diyl or 1,4-piperidyl;

$Z_1$ may be a direct bond, $CH_2CH_2$, COO, OOC, $O(CH_2)_3$, $OCH_2$, $CH_2O$, $(CH_2)_3O$, or $(CH_2)_4$;

$n_1$ may be 0 or 1;

W, Y may each independently be H, halogen, CN, alkyl with 1 to 12 carbon atoms which is optionally substituted with one or more fluorines;

$R_1$ may be H, halogen, CN, alkyl with 1 to 12 carbon atoms which is optionally substituted with one or more fluorines and in which optionally 1 or 2 non-adjacent methylene units ($CH_2$) can be replaced by oxygen, COO, OOC and/or a $CH_2CH_2$ group may be replaced by CH=CH;

or even more preferred structures for the groups $PG_{1-3}$ are given by the formula IIIA

IIIA wherein $A_4$ may be 1,4-phenylene, which is unsubstituted or substituted from one and up to and including all available substitution positions with one or more of the groups selected from halogen, CN, $NO_2$; or pyrimidine-2,5-diyl, pyridine-2,5-diyl, 2,5-thiophenediyl, 2,5-furanylene, 1,4- or 2,6-naphthalene;

$Z_3$ may be a direct bond, $CH_2CH_2$, COO, OOC, $O(CH_2)_3$, $OCH_2$, $CH_2O$, $(CH_2)_3O$, or $(CH_2)_4$;

$n_3$ may be 0 or 1;

$A_6$ may be $R_2$ may be alkyl with 1 to 12 carbon atoms which is optionally substituted with one or more fluorines and in which optionally 1 or 2 non-adjacent methylene units ($CH_2$) can be replaced by oxygen, COO, OOC and $CH_2CH_2$ may be replaced by CH=CH.

According to an aspect of this invention a method of providing an alignment layer on a surface of a liquid crystal cell wall includes the step of depositing a layer of a material comprising at least one compound of Formula I on the surface, followed by exposure to actinic radiation, and controlling the exposure time and/or intensity of radiation used to provide a selected value of pretilt in a liquid crystal placed in contact with the exposed layer.

The radiation includes light, with a wavelength of 250–450 nm. Preferably the radiation is light with a wavelength of 300–400 nm.

According to a further aspect of this invention a liquid crystal device comprises a layer of a liquid crystal material contained between two cell walls both carrying electrode structures and surface treated to provide an alignment layer for liquid crystal molecules;

characterised in that:

the surface treatment is a layer of material comprising a compound of Formula 1 which has been exposed to actinic radiation.

The radiation includes light, with a wavelength of 250–450 nm. Preferably the radiation is light with a wavelength of 300–400 nm.

Compounds of Formula I can be prepared by various routes from commercially available starting materials. Typically 1,2,3-trihydroxypropane (glycerol) can be esterified with ω-halogenoalkanoic acids in the presence of N,N-dicyclohexylcarbodiimide and 4-(dimethylamino)pyridine and a polar solvent, such as N,N-dimethylformamide or dichloromethane. The resultant bromides can then be alkylated in a Williams ether synthesis with a photoisomerisable/dimerisable group, such as 6-hydroxycoumarin, 7-hydroxycoumarin or alkyl 4-hydroxycinnamates, in the presence of a base, such as potassium carbonate, and a polar solvent, such as cyclohexanone or ethyl-methylketone. The bromides can also be esterified with a photoisomerisable/dimerisable group, such as cinnamic acids, in the presence of DBU and a non polar solvent, such as toluene or benzene. Similarly 1,2,3-trihydroxypropane (glycerol) can be alkylated with ω-halogenoalkanols protected, for example as the THP derivative, in the presence of base, such as potassium tert-butylate, and a polar solvent, such as 1,2-dimethoxyethane or ethylene glycol dimethyl ether. After deprotection the resultant alcohols can then be esterified with a photoisomerisable/dimerisable group, such as anthracene carboxylic acids or cinnamic acids, in the presence of N,N-dicyclohexylcarbodiimide and 4-(dimethylamino)pyridine and a polar solvent, such as N,N-dimethylformamide or dichloromethane. The alcohols can also be alkylated in a Mitsunobu reaction, with a photoisomerisable/dimerisable group, such as 6-hydroxycoumarin, 7-hydroxycoumarin or alkyl 4-hydroxycinnamates, in the presence of a dehydrating agent, such as diethyl azodicarboxylate and triphenyl phosphine, and a polar solvent, such as tetrahydrofuran or N,N-dimethylformamide.

The photocross-linkable groups, such as cinnamic acids, cinnamate esters, cinnamonitriles, styrenes, stilbenes, vinylnaphthalenes, vinylpyridines, maleimides, thymines, coumarins, anthracenes, are generally either commercially available or readily accessible, for example coumarin and cinnamate derivatives can be prepared according to literature methods, such as the Perkin, Pechmann, Wittig-Horner or Knoevenagel reactions. See J R Johnson, "The Perkin Reaction and Related Reactions", Organic Reactions, 1, 210–65, 1942; Wittig Horner Reaction: L Lombardo and R J K Taylor, Synthesis, 131, 1978; Knoevenagel Reaction: G Jones, Organic Reactions, 15, 204 (1967).

In order to obtain alignment layers in regions selectively limited by area, a solution of the photoactive propane derivative can, for example, firstly be prepared and then spread out using a spin-coating apparatus on a carrier coated with an electrode, e.g., a glass plate coated with indium-tin oxide (ITO) such that homogeneous layers of thickness typically in the range 50–200 nm result. Preferably the layers are in the range 0.05–50 $\mu$m. Subsequently or simultaneously, irradiation can be applied to the region to be isomerised and/or dimerised (cross-linked), e.g., with a mercury high pressure lamp, a xenon lamp or a UV laser utilising a polariser and optionally a mask for the formation of structures. The duration and irradiation depends on the capacity of the individual lamps and can vary from a few minutes to several hours. The cross-linking can, however, also be effected by irradiating the homogeneous layer using filters which, e.g., let through only radiation suitable for the cross-linking reaction. Photosensitisors, such as acetophenone or benzophenone may be added to shorten the illumination time required for cross-linking. Non-zero tilt angles ($\theta$) may be induced by illumination with plane polarised light from a non-perpendicular angle to the plane of the substrate.

The materials of the current invention when used in alignment layers are believed to be of particular benefit due to their lack of polydispersity.

The invention will now be described, by way of example only, with reference to the following examples and diagrams:

Figure 1:
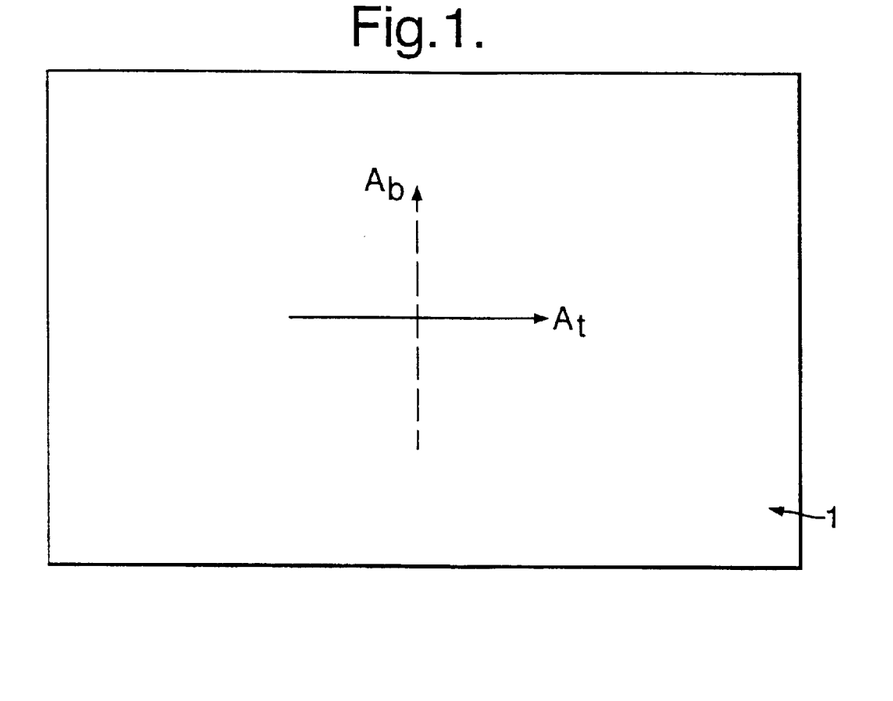
FIG. 1 is a plan view of a liquid crystal device.
Figure 2:
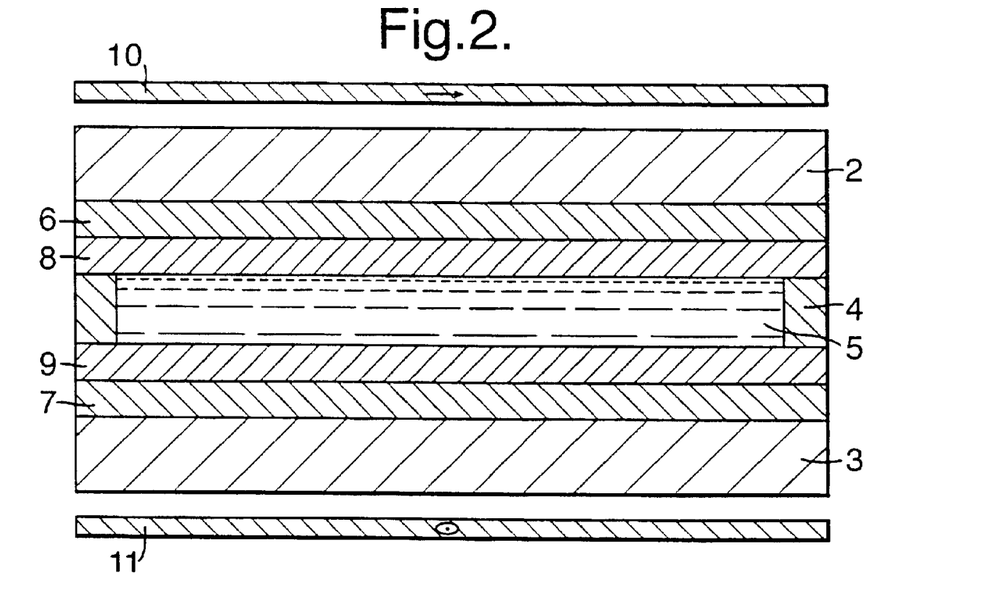
FIG. 2 is a cross sectional view of FIG. 1.

The device of FIGS. 1, 2 comprises a liquid crystal cell 1 formed by two cell walls 2, 3 spaced typically 1 to 15 $\mu$m apart by a spacer ring 4 to contain a layer 5 of a liquid crystal material. The inside faces of both walls 2, 3 are coated with an indium tin oxide layer 6, 7 forming transparent electrodes. The electrodes may be of sheet like form covering the complete wall, or formed into for example, strip electrodes to provide an array of addressable electrode intersections. The walls are also coated with an aligning layer 8, 9 of material described by the current invention. These layers provide both an alignment direction, indicated by $A_t$ and $A_b$ as orthogonally arranged.

If the material 5 is nematic then the device may be the known twisted nematic device. In this case polarisers 10, 11 are used to distinguish between the device voltage ON and OFF states.

The liquid crystal material may be nematic, cholesteric, or smectic material. The device may be used as a display device, e.g., displaying alpha numeric information, or an x, y matrix displaying information. Alternatively the device may operate as a shutter to modulate light transmission, e.g., as a spatial light modulator, or as a privacy window.

Figure 3:
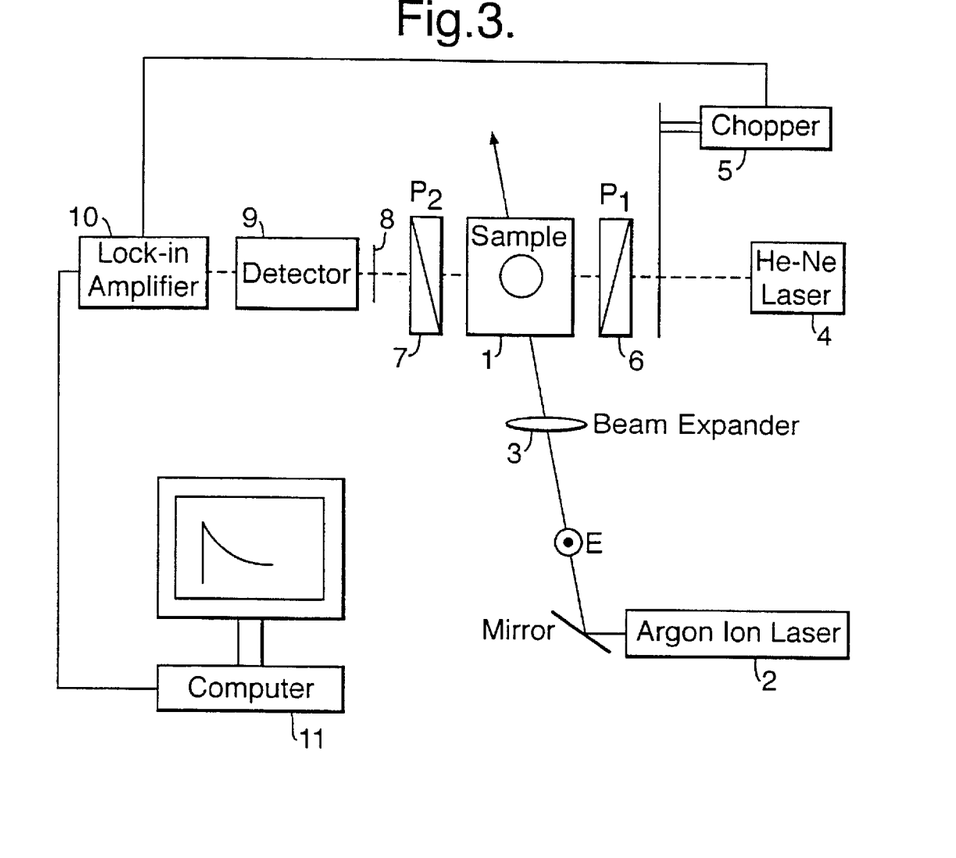
FIG. 3 is a schematic representation of the apparatus used to illuminate the photocross-linkable propane derivatives on a suitable substrate to be used as part of a liquid crystal device.
Figure 4:
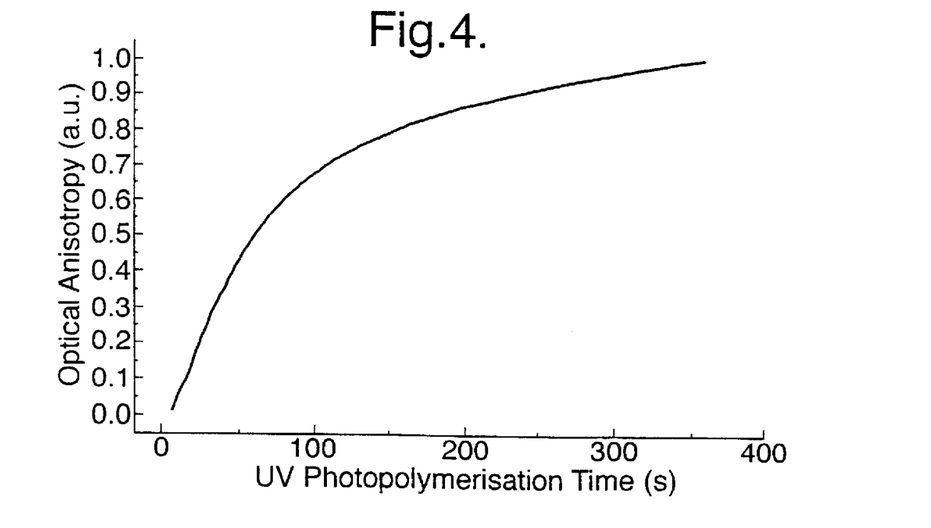
FIG. 4 is a typical plot of the induced optical anisotropy obtained for the object of the invention, in this case 1,2,3-tris[5-(4-(2-oxo-2H-1-benzopyran-7-yloxycarbonyl) phenoxy]pentanoyloxy)propane, on a fused silica substrate on illumination with plane polarised light at 300.5 nm.

The apparatus of FIG. 3 used to generate photoinduced anisotropy in the photoreactive sample 1 using linearly polarised UV light comprises a radiation source e.g. an argon ion laser 2 (Spectra Physics, Model 2045). The laser beam operating at 300.5 nm has a polarisation direction (E). The laser beam was expanded by using a quartz lens beam expander 3. The film anisotropy is measured by determining the induced birefringence against UV exposure time using a He—Ne laser 4 (632.8 nm) modulated by a rotating chopper 5. The probing wavelength does not perturb the anisotropy inducing process since it is far away from any intrinsic absorption band in either the starting material or photoproduct. During the UV exposure of the sample, the photoinduced birefringence was monitored using two crossed polarisers, P1 and P2, 6 and 7 arranged at +/−45° with respect to the vertical polarisation of the UV laser beam. The intensity of the beam from the probing He—Ne laser 4, which then passed through the sample, was detected by a photodetector 9. The birefringence measuring signal taken from the photodiode 9 was processed by a phase sensitive lock-in amplifier 10 and recorded by a computer 11. Data were plotted as birefringence versus UV exposure time.

The photocross-linkable propane derivatives and resultant alignment layers may be produced as described, by way of example only, in the following examples; K signifies the crystalline state, SmA signifies the smectic A phase, I signifies the isotropic phase, $T_g$ is the glass transition temperature.

EXAMPLE 1

Preparation of 1, 2, 3-tris[11-(4-[(E)-Ethoxycarbonylethenyl]phenoxy)undecanoyloxy] propane A mixture of 0.4 g 1, 2, 3-tris(11-bromoundecanoyloxy) propane, 2.9 g ethyl (E)-4-hydroxycinnamate, 20.0 g anhydrous potassium carbonate and 25 ml ethyl-methyl ketone was heated under gentle reflux overnight. The reaction mixture was filtered to remove inorganic material and the filtrate evaporated down. The residue was purified by column chromatography on silica gel using hexane/ethyl acetate (1/1 v/v) as eluent and recrystallisation from acetonitrile to yield 5.2 g of 1,2,3-tris[11-(4-[(E)-ethoxycarbonylethenyl]phenoxy)undecanoyloxy]propane.

The 1,2,3-tris(4-bromoundecanoyloxy)propane required as starting material was prepared as follows:

3.1 g Dicyclohexylcarbodiimide was added to a solution of 0.5 g 1,2,3-trihydroxy-propane (glycerol), 4.0 g 11-bromoundecanoic acid, 0.6 g 4-(dimethylamino)pyridine and 50 ml dichloromethane at 0° C. The reaction mixture was stirred overnight at room temperature, filtered to remove inorganic material and the filtrate evaporated down. The residue was purified by column chromatography on silica gel using hexane/ethyl acetate (1/1 v/v) as eluent and recrystallisation from acetonitrile to yield 0.4 g of 1,2,3-tris (11-bromoundecanoyloxy)propane.

The ethyl (E)-4-hydroxycinnamate required as starting material was prepared as follows:

A mixture of 10 g 4-hydroxycinnamic acid, 100 ml ethanol and 0.5 ml concentrated sulphuric acid was heated under gentle reflux for 96 hours. The reaction mixture was poured onto water, the resultant precipitate filtered off, washed with portions of water and then dried. The residue was purified by column chromatography on silica gel using ethyl acetate as eluent and recrystallisation from acetonitrile to yield 9.2 g of ethyl (E)-4-hydroxycinnamate.

The following compounds can be prepared in an analogous manner:

1,2,3-tris[3-(4-[(E)-methoxycarbonylethenyl]phenoxy)propanoyloxy]propane.

1,2,3-tris[4-(4-[(E)-methoxycarbonylethenyl]phenoxy)butanoyloxy]propane.

1,2,3-tris[5-(4-[(E)-methoxycarbonylethenyl]phenoxy)pentanoyloxy]propane.

1,2,3-tris[6-(4-[(E)-methoxycarbonylethenyl]phenoxy)hexanoyloxy]propane.

1,2,3-tris[7-(4-[(E)-methoxycarbonylethenyl]phenoxy)heptanoyloxy]propane.

1,2,3-tris[8-(4-[(E)-methoxycarbonylethenyl]phenoxy)octanoyloxy]propane.

1,2,3-tris[9-(4-[(E)-methoxycarbonylethenyl]phenoxy)nonanoyloxy]propane.

1,2,3-tris[10-(4-[(E)-methoxycarbonylethenyl]phenoxy)decanoyloxy]propane.

1,2,3-tris[11-(4-[(E)-methoxycarbonylethenyl]phenoxy)undecanoyloxy]propane.

1,2,3-tris[12-(4-[(E)-methoxycarbonylethenyl]phenoxy)dodecanoyloxy]propane.

1,2,3-tris[3-(4-[(E)-ethoxycarbonylethenyl]phenoxy)propanoyloxy]propane.

1,2,3-tris[4-(4-[(E)-ethoxycarbonylethenyl]phenoxy)butanoyloxy]propane.

1,2,3-tris[5-(4-[(E)-ethoxycarbonylethenyl]phenoxy)pentanoyloxy]propane.

1,2,3-tris[6-(4-[(E)-ethoxycarbonylethenyl]phenoxy)hexanoyloxy]propane.

1,2,3-tris[7-(4-[(E)-ethoxycarbonyiethenyl]phenoxy)heptanoyloxy]propane.

1,2,3-tris[8-(4-[(E)-ethoxycarbonylethenyl]phenoxy)octanoyloxy]propane.

1,2,3-tris[9-(4-[(E)-ethoxycarbonylethenyl]phenoxy)nonanoyloxy]propane.

1,2,3-tris[10-(4-[(E)-ethoxycarbonylethenyl]phenoxy)decanoyioxy]propane.

1,2,3-tris[12-(4-[(E)-ethoxycarbonylethenyl]phenoxy)dodecanoyloxy]propane.

1,2,3-tris[6-(4-[(E)-ethoxycarbonylethenyl]biphenyl-4'-yloxy)hexyloxy]propane, K, 169° C.

1,2,3-tris(3-[2-oxo-2H-1-benzopyran-7-yloxy]propanoyloxy)propane.

1,2,3-tris(4-[2-oxo-2H-1-benzopyran-7-yloxy]butanoyloxy)propane.

1,2,3-tris(5-[2-oxo-2H-1-benzopyran-7-yloxy]pentanoyloxy)propane, $T_g$, −10° C.

1,2,3-tris(6-[2-oxo-2H-1-benzopyran-7-yloxy]hexanoyloxy)propane.

1,2,3-tris(7-[2-oxo-2H-1-benzopyran-7-yloxy]heptanoyloxy)propane.

1,2,3-tris(8-[2-oxo-2H-1-benzopyran-7-yloxy]octanoyloxy)propane.

1,2,3-tris(9-[2-oxo-2H-1-benzopyran-7-yloxy]nonanoyloxy)propane.

1,2,3-tris(10-[2-oxo-2H-1-benzopyran-7-yloxy]decanoyloxy)propane.

1,2,3-tris(11-[2-oxo-2H-1-benzopyran-7-yloxy]undecanoyloxy)propane.

1,2,3-tris(12-[2-oxo-2H-1-benzopyran-6-yloxy]heptanoyloxy)propane.

EXAMPLE 2

Preparation of 1,2,3-tris(10-[4-(2-oxo-2H-1-benzopyran-7-yloxycarbonyl)phenoxy]decanoyloxy)propane 0.77 g Dicyclohexylcarbodiimide is added to a solution of 0.56 g 7-hydroxycoumarin, 1.0 g 1,2,3-tris(1-[4-carboxyphenoxy]decanoyloxy)propane, 0.1 g 4-(dimethylamino)pyridine and 25 ml dichloromethane at 0° C. The reaction mixture is stirred overnight at room temperature, filtered to remove inorganic material and the filtrate evaporated down. The residue is purified by column chromatography on silica gel using hexane/ethyl acetate (1/1 v/v) as eluent and recrystallisation from acetonitrile to yield 0.4 g of 1,2,3-tris(10-[4-(2-oxo-2H-1-benzopyran-7-yloxycarbonyl)phenoxy]decanoyloxy)propane.

The 1,2,3-tris(10-[4-carboxyphenoxy]decanoyloxy)propane required as starting material is prepared as follows:

A mixture of 10.0 g 1,2,3-tris(10-bromodecanoyloxy)propane, 4.6 g 4-hydroxybenzaldehyde, 52.4 g anhydrous potassium carbonate and 250 ml ethyl-methyl ketone is heated under gentle reflux overnight. The reaction mixture is filtered to remove inorganic material and the filtrate evaporated down. The residue is purified by column chromatography on silica gel using hexane/ethyl acetate (1/1 v/v) as eluent and recrystallisation from acetonitrile to yield 8.1 g of 1,2,3-tris(10-[4formylphenoxy]decanoyloxy)propane.

10 ml of a solution of Jones' reagent is added dropwise at 0° C. to a mixture of 8.1 g 1,2,3-tris(10-[4-formylphenoxy]decanoyloxy)propane in 25 ml acetone. The reaction mixture is stirred at room temperature for 2 hours, poured onto water and the resultant precipitate filtered off, washed with portions of water and dried. The solid product is purified by recrystallisation from ethyl acetate to yield 3.7 g of 1,2,3-tris(10-[4-carboxyphenoxy]decanoyloxy)propane.

The following compounds can be prepared in an analogous manner:

1,2,3-tris(3-[4-(2-oxo-2H-1-benzopyran-7-yloxycarbonyl)phenoxy]propanoyloxy)propane.

1,2,3-tris(4-[4-(2-oxo-2H-1-benzopyran-7-yloxycarbonyl)phenoxy]butanoyloxy)propane.

1,2,3-tris(5-[4-(2-oxo-2H-1-benzopyran-7-yloxycarbonyl)phenoxy]pentanoyloxy)propane.

1,2,3-tris(6-[4-(2-oxo-2H-1-benzopyran-7-yloxycarbonyl)phenoxy]hexanoyloxy)propane.

1,2,3-tris(7-[4-(2-oxo-2H-1-benzopyran-7-yloxycarbonyl)phenoxy]heptanoyloxy)propane.

1,2,3-tris(8-[4-(2-oxo-2H-1-benzopyran-7-yloxycarbonyl)phenoxy]octanoyloxy)propane.

1,2,3-tris(9-[4-(2-oxo-2H-1-benzopyran-7-yloxycarbonyl)phenoxy]nonanoyloxy)propane.

1,2,3-tris(11-[4-(2-oxo-2H-1-benzopyran-7-yloxycarbonyl)phenoxy]undecanoyloxy)propane.

1,2,3-tris(7-[4-(2-oxo-2H-1-benzopyran-6-yloxycarbonyl)phenoxy]heptanoyloxy)propane.

1,2,3-tris(10-[2-fluoro-4-(2-oxo-2H-1-benzopyran-7-yloxycarbonyl)phenoxy]decanoyloxy)propane.

1,2,3-tris(10-[2-chloro-4-(2-oxo-2H-1-benzopyran-7-yloxycarbonyl)phenoxy]decanoyloxy)propane.

1,2,3-tris(10-[2-bromo-4-(2-oxo-2H-1-benzopyran-7-yloxycarbonyl)phenoxy]decanoyloxy)propane.

1,2,3-tris(10-[2-cyano-4-(2-oxo-2H-1-benzopyran-7-yloxycarbonyl)phenoxy]decanoyloxy)propane.

1,2,3-tris(10-[2-methoxy-4-(2-oxo-2H-1-benzopyran-7-yloxycarbonyl)phenoxy]decanoyloxy)propane.

1,2,3-tris(10-[3-fluoro-4-(2-oxo-2H-1-benzopyran-7-yloxycarbonyl)phenoxy]decanoyloxy)propane.

1,2,3-tris(10-[3-chloro-4-(2-oxo-2H-1-benzopyran-7-yloxycarbonyl)phenoxy]decanoyloxy)propane.

1,2,3-tris(10-[3-bromo-4-(2-oxo-2H-1-benzopyran-7-yloxycarbonyl)phenoxy]decanoyloxy)propane.

1,2,3-tris(10-[3-cyano-4-(2-oxo-2H-1-benzopyran-7-yloxycarbonyl)phenoxy]decanoyloxy)propane.

1,2,3-tris(10-[3-methoxy-4-(2-oxo-2H-1-benzopyran-7-yloxycarbonyl)phenoxy]decanoyloxy)propane.

1,2,3-tris(10-[2,3-difluoro-4-(2-oxo-2H-1-benzopyran-7-yloxycarbonyl)phenoxy]decanoyloxy)propane.

1,2,3-tris(10-[2,3-chloro-4-(2-oxo-2H-1-benzopyran-7-yloxycarbonyl)phenoxy]decanoyloxy)propane.

1,2,3-tris(10-[2,3-bromo-4-(2-oxo-2H-1-benzopyran-7-yloxycarbonyl)phenoxy]decanoyloxy)propane.

EXAMPLE 3

Preparation of 1,2,3-tris(10-[4-(4-cyano-4'-biphenyloxycarbonylethenyl)phenoxy]decanoyloxy)propane 0.7 g Dicyclohexylcarbodiimide is added to a solution of 0.6 g 4-cyano-4'-hydroxybiphenyl, 1.0 g 1,2,3-tris(10-[4-(carboxyethenyl)phenoxy]decanoyloxy)propane, 0.1 g 4-dimethylaminopyridine and 50 ml dichloromethane at 0° C. The reaction mixture is stirred overnight at room temperature, filtered to remove inorganic material and the filtrate evaporated down. The residue is purified by column chromatography on silica gel using hexane/ethyl acetate (1/1 v/v) as eluent and recrystallisation from acetonitrile to yield 0.4 g of 1,2,3-tris(10-[4-(4-cyano-4'-biphenyloxycarbonylethenyl)phenoxy]decanoyloxy) propane.

The 1,2,3-tris(10-[4-(carboxyethenyl)phenoxy] decanoyloxy)propane required as starting material is prepared as follows:

4 ml of a 1.6 mol ml$^{-1}$ solution of butyllithium is added dropwise at 0° C. under an atmosphere of nitrogen to a solution of 1.7 g trimethylsilyl P,P-diethylphosphonoacetate in 100 ml tetrahydrofuran. The reaction mixture is stirred at room temperature for 3 hours and then a solution of 5.0 g 1,2,3-tris(10-[4-formylphenoxy]decanoyloxy)propane in 50 ml tetrahydrofuran is added dropwise. The solution is stirred at room temperature overnight, reduced in volume under reduced pressure, then poured onto 500 ml water. The aqueous layer is acidified (pH 1) with hydrochloric acid and then extracted into ethyl acetate (3×100 ml). The combined organic layers are washed with brine (2×500 ml), dried over anhydrous magnesium sulphate, filtered, and the filtrate evaporated down. The residue is purified by recrystallisation from acetonitrile to yield 2.3 g of 1,2,3-tris(10-[4-(carboxyethenyl)phenoxy]decanoyloxy)propane.

The following compounds can be prepared in an analogous manner:

3-tris(3-[4-(4-cyano-4'-biphenyloxycarbonylethenyl)phenoxy]propanoyloxy)propane.

3-tris(4-[4-(4-cyano-4'-biphenyloxycarbonylethenyl)phenoxy]butanoyloxy)propane.

3-tris(5-[4-(4-cyano-4'-biphenyloxycarbonylethenyl)phenoxy]pentanoyloxy)propane.

3-tris(6-[4-(4-cyano-4'-biphenyloxycarbonylethenyl)phenoxy]hexanoyloxy)propane.

3-tris(7-[4-(4-cyano-4'-biphenyloxycarbonylethenyl)phenoxy]heptanoyloxy)propane.

3-tris(8-[4-(4-cyano-4'-biphenyloxycarbonylethenyl)phenoxy]octanoyloxy)propane.

3-tris(9-[4-(4-cyano-4'-biphenyloxycarbonylethenyl)phenoxy]nonanoyloxy)propane.

3-tris(11-[4-(4-cyano4'-biphenyloxycarbonylethenyl)phenoxy]undecanoyloxy)propane.

3-tris(1 2-[4-(4-cyano-4'-biphenyloxycarbonylethenyl)phenoxy]dodecanoyloxy)propane.

3-tris(10-[4-(4-cyano-phenoxycarbonylethenyl)phenoxy]decanoyloxy)propane.

3-tris(10-[4-(4-cyano-3-fluoro-phenoxycarbonylethenyi)phenoxy]decanoyloxy)propane.

3-tris(10-[4-(4-cyano-2-fluoro-phenoxycarbonylethenyl)phenoxy]decanoyloxy)propane.

3-tris(10-[4-(4-[5-pentylpyrimidin-2-yl]-phenoxycarbonylethenyl)phenoxy]decanoyloxy)propane.

3-tris(10-[4-(4-[5-pentylpyridin-2-yl]-phenoxycarbonylethenyl)phenoxy]decanoyloxy)propane.

3-tris(10-[4-(4-[2-pentylpyrimidin-5-yl]-phenoxycarbonylethenyl)phenoxy]decanoyloxy)propane.

3-tris(10-[4-(4-[2-pentylpyridin-5-yl]-phenoxycarbonylethenyl)phenoxy]decanoyloxy)propane.

3-tris(10-[4-(4-[trans-4-pentylcyclohexyl]-phenoxycarbonylethenyl)phenoxy]decanoyloxy)propane.

3-tris(10-[4-(trans-4-[trans-4-pentylcyclohexyl]-cyclohexyloxycarbonylethenyl)phenoxy]decanoyloxy)propane.

EXAMPLE 4

Preparation of 1,2,3-tris(10-[4-Fluorophenylacryloyloxy]decanoyloxy)propane

A solution of 0.7 g 4-fluorocinnamic acid, 1.0 g 1,2,3-tris (10-bromodecanoyloxy)propane, 0.6 g 1,8-diazabicyclo [5.4.0]undec-7-ene (DBU) and 25 ml toluene is heated under gentle reflux overnight. The reaction mixture is washed with water (2×100 ml), dried over magnesium sulphate, filtered to remove inorganic material and the filtrate evaporated down.

The residue is purified by column chromatography on silica gel using hexane/ethyl acetate (1/1 v/v) as eluent and recrystallisation from acetonitrile to yield 0.4 g of 1,2,3-tris (10-[4-fluorophenylacryloyloxy]decanoyloxy)propane.

The following compounds can be prepared in an analogous manner:

1,2,3-tris(5-[4-fluorophenylacryloyloxy]pentanoyloxy) propane.
1,2,3-tris(6-[4-fluorophenylacryloyloxy]hexanoyloxy) propane.
1,2,3-tris(7-[4-fluorophenylacryloyioxy]heptanoyloxy) propane.
1,2,3-tris(8-[4-fluorophenylacryloyloxy]octanoyloxy) propane.
1,2,3-tris(9-[4-fluorophenylacryloyloxy]nonanoyloxy) propane.
1,2,3-tris(10-[4-chlorophenylacryloyloxy]decanoyloxy) propane.
1,2,3-tris(10-[4-bromophenylacryloyloxy]decanoyloxy) propane.
1,2,3-tris(10-[4-cyanophenylacryloyloxy]decanoyloxy) propane.
1,2,3-tris(10-[4-cyano-4'-biphenylacryloyloxy] decanoyloxy)propane.
1,2,3-tris(10-[4-methoxy-4'-biphenylacryloyloxy] decanoyloxy)propane.
1,2,3-tris(10-[4-ethoxy-4'-biphenylacryloyloxy] decanoyloxy)propane.
1,2,3-tris(10-[4-propyloxy-4'-biphenylacryloyloxy] decanoyloxy)propane.
1,2,3-tris(10-[4-butyloxy-4'-biphenylacryloyloxy] decanoyloxy)propane.
1,2,3-tris(10-[4-pentyloxy-4'-biphenylacryloyloxy] decanoyloxy)propane.
1,2,3-tris(10-[4-hexyoxy-4'-biphenylacryloyloxy] decanoyloxy)propane.
1,2,3-tris(10-[4-heptoxy-4'-biphenylacryloyloxy] decanoyloxy)propane.
1,2,3-tris(10-[4-octyloxy-4'-biphenylacryloyloxy] decanoyloxy)propane.
1,2,3-tris(10-[4-(trans-4-pentylcyclohexyl) phenylacryloyloxy]decanoyloxy)propane.
1,2,3-tris(10-[anthracene-2-carbonyloxy]decanoyloxy) propane.
1,2,3-tris(10-[anthracene-9-carbonyloxy]decanoyloxy) propane.

EXAMPLE 5

Preparation of 1,2,3-tris(10-[2-oxo-2H-1-Benzopyran-7-yloxy]decyloxy)propane 0.7 g Diethyl azodicarboxylate is added to a solution of 0.7 g 7-hydroxycoumarin, 0.7 g 1,2,3-tris(10-hydroxydecyloxy)propane, 1.1 g triphenyl phosphine and 50 ml tetrahydrofuran at 0° C. The reaction mixture is stirred overnight at room temperature and then evaporated down with silica gel. The resultant powder is purified by column chromatography on silica gel using hexane/ethyl acetate (1/1 v/v) as eluent and recrystallisation from acetonitrile to yield 0.35 g of 1,2,3-tris(10-[2-oxo-2H-1-benzopyran-7-yloxycarbonyl]decyloxy)propane.

The 1,2,3-tris(10-hydroxydecyloxy)propane required as starting material is prepared as follows:

A mixture of 100 g 1-bromodecan-10-ol, 2.1 g bis(trimethylsilyl)sulphate, 43 g 3,4-dihydro-2H-pyran and 500 ml dichloromethane is stirred for 6 hours at room temperature. Several drops of pyridine are added and the reaction mixture evaporated down. The residue is purified by column chromatography on silica gel using hexane/ethyl acetate (1/1 v/v) as eluent to yield 58 g of 1-bromo-10-[tetrahydropyranyloxy]decane.

A mixture of 58 g 1-bromo-10-[tetrahydropyranyloxy] decane, 5 g 1,2,3-trihydroxypropane (glycerol), 74 g potassium tert.-butoxide and 500 ml 1,2-dimethoxyethane is stirred at room temperature overnight. The reaction mixture is added to water and extracted into ethyl acetate (3×100 ml). The combined organic layers are washed with water (2×500 ml), dried over magnesium sulphate, filtered and the filtrate then evaporated down. The residue is purified by column chromatography on silica gel using hexane/ethyl acetate (1/1 v/v) as eluent and recrystallisation from acetonitrile to yield 13 g of 1,2,3-tris(10-[tetrahydropyranyloxy] decyloxy)propane.

A mixture of 13 g 1,2,3-tris(10-[tetrahydropyranyloxy] decyloxy)propane, 1 g bis(trimethylsilyl)sulphate and 250 ml methanol is stirred at room temperature for 2 hours. The reaction mixture is evaporated down. The residue is purified by column chromatography on silica gel using hexane/ethyl acetate (1/1 v/v) as eluent and recrystallisation from acetonitrile to yield 7.1 g of 1,2,3-tris(10-hydroxydecyloxy) propane.

The following compounds can be prepared in an analogous manner:

1,2,3-tris(3-[2-oxo-2H-1-benzopyran-7-yloxy] propyloxy)propane.
1,2,3-tris(5-[2-oxo-2H-1-benzopyran-7-yloxy]pentyloxy) propane.
1,2,3-tris(6-[2-oxo-2H-1-benzopyran-7-yloxy]hexyloxy) propane.
1,2,3-tris(7-[2-oxo-2H-1-benzopyran-7-yloxy]heptyloxy) propane.
1,2,3-tris(8-[2-oxo-2H-1-benzopyran-7-yloxy]octyloxy) propane.
1,2,3-tris(9-[2-oxo-2H-1-benzopyran-7-yloxy]nonyloxy) propane.
1,2,3-tris(11-[2-oxo-2H-1-benzopyran-7-yloxy] undecyloxy)propane.
1,2,3-tris(12-[2-oxo-2H-1-benzopyran-7-yloxy] dodecyloxy)propane.
1,2,3-tris[3-(4-[(E)-methoxycarbonylethenyl]phenoxy) propyloxy]propane.
1,2,3-tris[4-(4-[(E)-methoxycarbonylethenyl]phenoxy) butyloxy]propane.
1,2,3-tris[5-(4-[(E)-methoxycarbonylethenyl]phenoxy) pentyloxy]propane.
1,2,3-tris[6-(4-[(E)-methoxycarbonylethenyl]phenoxy) hexyloxy]propane.
1,2,3-tris[7-(4-[(E)-methoxycarbonylethenyl]phenoxy) heptyloxy]propane.
1,2,3-tris[8-(4-[(E)-methoxycarbonylethenyl]phenoxy) octyloxy]propane.
1,2,3-tris[9-(4-[(E)-methoxycarbonylethenyl]phenoxy) nonyloxy]propane.
1,2,3-tris[11-(4-[(E)-methoxycarbonylethenyl]phenoxy) decyloxy]propane.
1,2,3-tris[11-(4-[(E)-methoxycarbonylethenyl]phenoxy) undecyloxy]propane.

1,2,3-tris[12-(4-[(E)-methoxycarbonylethenyl]phenoxy) dodecyloxy]propane.
1,2,3-tris[3-(4-[(E)-ethoxycarbonylethenyl]phenoxy) propyloxy]propane.
1,2,3-tris[4-(4-[(E)-ethoxycarbonylethenyl]phenoxy) butyloxy]propane.
1,2,3-tris[5-(4-[(E)-ethoxycarbonylethenyl]phenoxy) pentyloxy]propane.
1,2,3-tris[6-(4-[(E)-ethoxycarbonylethenyl]phenoxy) hexyloxy]propane.
1,2,3-tris[7-(4-[(E)-ethoxycarbonylethenyl]phenoxy) heptyloxy]propane.
1,2,3-tris[8-(4-[(E)-ethoxycarbonylethenyl]phenoxy) octyloxy]propane.
1,2,3-tris[9-(4-[(E)-ethoxycarbonylethenyl]phenoxy) nonyloxy]propane.
1,2,3-tris[11-(4-[(E)-ethoxycarbonylethenyl]phenoxy) decyloxy]propane.
1,2,3-tris[11-(4-[(E)-ethoxycarbonylethenyl]phenoxy) undecyloxy]propane.
1,2,3-tris[12-(4-[(E)-ethoxycarbonylethenyl]phenoxy) dodecyloxy]propane.

EXAMPLE 6

Preparation of 1,2,3-tris(10-[4-(2-oxo-2H-1-Benzopyran-7-yloxycarbonyl)phenoxy]decyloxy) propane 0.81 g Dicyclohexylcarbodiimide is added to a solution of 0.58 g 7-hydroxycoumarin, 1.0 g 1,2,3-tris(10-[4-carboxyphenoxy]decyloxy)propane, 0.1 g 4-dimethylaminopyridine and 50 ml dichloromethane at 0° C. The reaction mixture is stirred overnight at room temperature, filtered to remove inorganic material and the filtrate evaporated down. The residue is purified by column chromatography on silica gel using hexane/ethyl acetate (1/1 v/v) as eluent and recrystallisation from acetonitrile to yield 0.4 g of 1,2,3-tris(10-[4-(2-oxo-2H-1-benzopyran-7-yloxycarbonyl)phenoxy]decyloxy)propane.

The 1,2,3-tris(10-[4-carboxyphenoxy]decyloxy)propane required as starting material is prepared as follows:

5.1 g Diethyl azodicarboxylate is added to a solution of 3.6 g 4-hydroxybenzaldehyde, 5.0 g 1,2,3-tris(10-hydroxydecyloxy)propane, 7.7 g triphenyl phosphine and 100 ml tetrahydrofuran at 0° C. The reaction mixture is stirred overnight at room temperature and then evaporated down with silica gel. The resultant powder is purified by column chromatography on silica gel using hexane/ethyl acetate (1/1 v/v) as eluent and recrystallisation from acetonitrile to yield 4.7 g of 1,2,3-tris(10-[4-formylphenoxy] decyloxy)propane.

6 ml of a solution of Jones' reagent is added dropwise at 0° C. to a mixture of 4.7 g 1,2,3-tris(10-[4-formylphenoxy] decyloxy)propane in 100 ml acetone. The reaction mixture is stirred at room temperature for 2 hours, poured onto water and the resultant precipitate filtered off, washed with portions of water and dried. The solid product is purified by recrystallisation from ethyl acetate to yield 2.2 g of 1,2,3-tris(10-[4-carboxyphenoxy]decyloxy)propane.

The following compounds can be prepared in an analogous manner:

1,2,3-tris(3-[4-(2-oxo-2H-1-benzopyran-7-yloxycarbonyl)phenoxy]propyloxy)propane.
1,2,3-tris(4-[4-(2-oxo-2H-1-benzopyran-7-yloxycarbonyl)phenoxy]butyloxy)propane.
1,2,3-tris(5-[4-(2-oxo-2H-1-benzopyran-7-yloxycarbonyl)phenoxy]pentyloxy)propane.
1,2,3-tris(6-[4-(2-oxo-2H-1-benzopyran-7-yloxycarbonyl)phenoxy]hexyloxy)propane.
1,2,3-tris(7-[4-(2-oxo-2H-1-benzopyran-7-yloxycarbonyl)phenoxy]heptyloxy)propane.
1,2,3-tris(8-[4-(2-oxo-2H-1-benzopyran-7-yloxycarbonyl)phenoxy]octyloxy)propane.
1,2,3-tris(9-[4-(2-oxo-2H-1-benzopyran-7-yloxycarbonyl)phenoxy]nonyloxy)propane.
1,2,3-tris(11-[4-(2-oxo-2H-1-benzopyran-7-yloxycarbonyl)phenoxy]undecyloxy)propane.
1,2,3-tris(12-[4-(2-oxo-2H-1-benzopyran-7-yloxycarbonyl)phenoxy]dodecyloxy)propane.
1,2,3-tris(10-[2-fluoro-4-(2-oxo-2H-1-benzopyran-7-yloxycarbonyl)phenoxy]decyloxy)propane.
1,2,3-tris(10-[2-chloro-4-(2-oxo-2H-1-benzopyran-7-yloxycarbonyl)phenoxy]decyloxy)propane.
1,2,3-tris(10-[2-bromo-4-(2-oxo-2H-1-benzopyran-7-yloxycarbonyl)phenoxy]decyloxy)propane.
1,2,3-tris(10-[2-cyano-4-(2-oxo-2H-1-benzopyran-7-yloxycarbonyl)phenoxy]decyloxy)propane.
1,2,3-tris(10-[2-methoxy-4-(2-oxo-2H-1-benzopyran-7-yloxycarbonyl)phenoxy]decyloxy)propane.
1,2,3-tris(10-[3-fluoro-4-(2-oxo-2H-1-benzopyran-7-yloxycarbonyl)phenoxy]decyloxy)propane.
1,2,3-tris(10-[3-chloro-4-(2-oxo-2H-1-benzopyran-7-yloxycarbonyl)phenoxy]decyloxy)propane.
1,2,3-tris(10-[3-bromo-4-(2-oxo-2H-1-benzopyran-7-yloxycarbonyl)phenoxy]decyloxy)propane.
1,2,3-tris(10-[3-cyano-4-(2-oxo-2H-1-benzopyran-7-yloxycarbonyl)phenoxy]decyloxy)propane.
1,2,3-tris(10-[3-methoxy4-(2-oxo-2H-1-benzopyran-7-yloxycarbonyl)phenoxy]decyloxy)propane.
1,2,3-tris(10-[2,3-difluoro-4-(2-oxo-2H-1-benzopyran-7-yloxycarbonyl)phenoxy]decyloxy)propane.
1,2,3-tris(10-[2,3-chloro-4-(2-oxo-2H-1-benzopyran-7-yloxycarbonyl)phenoxy]decyloxy)propane.
1,2,3-tris(10-[2,3-bromo-4-(2-oxo-2H-1-benzopyran-7-yloxycarbonyl)phenoxy]decyloxy)propane.

EXAMPLE 7

Preparation of 1,2,3-tris(10-[4-(4-Cyano-4'-biphenyloxycarbonylethenyl)phenoxy]decyloxy) propane 0.7 g Dicyclohexylcarbodiimide is added to a solution of 0.6 g 4-cyano-4'-hydroxybiphenyl, 1.0 g 1,2,3-tris(10-[4-(carboxyethenyl)phenoxy]decyloxy)propane, 0.1 g 4-dimethylaminopyridine and 50 ml dichloromethane at 0° C. The reaction mixture is stirred overnight at room temperature, filtered to remove inorganic material and the filtrate evaporated down. The residue is purified by column chromatography on silica gel using hexane/ethyl acetate (1/1 v/v) as eluent and recrystallisation from acetonitrile to yield 0.4 g of 1,2,3-tris(10-[4-(4-cyano-4'-biphenyloxycarbonylethenyl)phenoxy]decyloxy)propane.

The 1,2,3-tris(10-[4-(carboxyethenyl)phenoxy]decyloxy) propane required as starting material is prepared as follows:

4 ml of a 1.6 mol ml$^{-1}$ solution of butyllithium is added dropwise at 0° C. under an atmosphere of nitrogen to a solution of 1.7 g trimethylsilyl P,P-diethylphosphonoacetate in 100 ml tetrahydrofuran. The reaction mixture is stirred at room temperature for 3 hours and then a solution of 5.0 g 1,2,3-tris(10-[4-formylphenoxy]decyloxy)propane in 50 ml tetrahydrofuran is added dropwise. The solution is stirred at room temperature overnight, reduced in volume under reduced pressure, then poured onto 500 ml water. The aqueous layer is acidified (pH 1) with hydrochloric acid and then extracted into ethyl acetate (3×100 ml). The combined organic layers are washed with brine (2×500 ml), dried over anhydrous magnesium sulphate, filtered, and the filtrate evaporated down. The residue is purified by recrystallisation from acetonitrile to yield 2.5 g of 1,2,3-tris(10-[4-(carboxyethenyl)phenoxy]decyloxy)propane.

The following compounds can be prepared in an analogous manner:

- 3-tris(3-[4-(4-cyano4'-biphenyloxycarbonylethenyl)phenoxy]propyloxy) propane.
- 3-tris(4-[4-(4-cyano-4'-biphenyloxycarbonylethenyl)phenoxy]butyloxy)propane.
- 3-tris(5-[4-(4-cyano-4'-biphenyloxycarbonylethenyl)phenoxy]pentyloxy)propane.
- 3-tris(6-[4-(4-cyano-4'-biphenyloxycarbonylethenyl)phenoxy]hexyloxy)propane.
- 3-tris(7-[4-(4-cyano-4'-biphenyloxycarbonylethenyi)phenoxy]heptyloxy)propane.
- 3-tris(8-[4-(4-cyano-4'-biphenyloxycarbonylethenyl)phenoxy]octyloxy)propane.
- 3-tris(9-[4-(4-cyano-4'-biphenyloxycarbonylethenyl)phenoxy]nonyloxy)propane.
- 3-tris(11-[4-(4-cyano-4'-biphenyloxycarbonylethenyl)phenoxy]undecyloxy)propane.
- 3-tris(12-[4-(4-cyano-4'-biphenyloxycarbonylethenyl)phenoxy]dodecyloxy)propane.
- 3-tris(10-[4-(4-cyano-phenoxycarbonylethenyl)phenoxy]decyloxy)propane.
- 3-tris(10-[4-(4-cyano-3-fluoro-phenoxycarbonylethenyl)phenoxy]decyloxy)propane.
- 3-tris(10-[4-(4-cyano-2-fluoro-phenoxycarbonylethenyl)phenoxy]decyloxy)propane.
- 3-tris(10-[4-(4-[5-pentylpyrimidin-2-yl]-phenoxycarbonylethenyl)phenoxy]decyloxy)propane.
- 3-tris(10-[4-(4-[5-pentylpyridin-2-yl]-phenoxycarbonylethenyl)phenoxy]decyloxy)propane.
- 3-tris(10-[4-(4-[2-pentylpyrimidin-5-yl]-phenoxycarbonylethenyl)phenoxy]decyloxy)propane.
- 3-tris(10-[4-(4-[2-pentylpyridin-5-yl]-phenoxycarbonylethenyl)phenoxy]decyloxy)propane.
- 3-tris(10-[4-(4-[trans-4-pentylcyclohexyl]-phenoxycarbonylethenyl)phenoxy]decyloxy)propane.
- 3-tris(10-[4-(trans-4-[trans-4-pentylcyclohexyl]-cyclohexyloxycarbonylethenyl)phenoxy]decyloxy)propane.

EXAMPLE 8

Preparation of 1,2,3-tris(10-[4-Fluorophenylacryloyloxy]decyloxy)propane 1.3 g Dicyclohexylcarbodiimide is added to a solution of 1.0 g 4-fluorocinnamic acid, 1.0 g 1,2,3-tris(10-hydroxydecyloxy)propane, 0.07 g 4-dimethylaminopyridine and 50 ml dichloromethane at 0° C. The reaction mixture is stirred overnight at room temperature, filtered to remove inorganic material and the filtrate evaporated down. The residue is purified by column chromatography on silica gel using hexane/ethyl acetate (1/1 v/v) as eluent and recrystallisation from acetonitrile to yield 0.8 g of 1,2,3-tris(10-[4-fluorophenylacryloyloxy]decyloxy)propane.

The following compounds can be prepared in an analogous manner:

- 1,2,3-tris(5-[4-fluorophenylacryloyloxy]pentyloxy)propane.
- 1,2,3-tris(6-[4-fluorophenylacryloyloxy]hexyloxy)propane.
- 1,2,3-tris(7-[4-fluorophenylacryloyloxy]heptyloxy)propane.
- 1,2,3-tris(8-[4-fluorophenylacryloyloxy]octyloxy)propane.
- 1,2,3-tris(9-[4-fluorophenylacryloyloxy]nonyloxy)propane.
- 1,2,3-tris(10-[4-chlorophenylacryloyloxy]decyloxy)propane.
- 1,2,3-tris(10-[4-bromophenylacryloyloxy]decyloxy)propane.
- 1,2,3-tris(10-[4-cyanophenylacryloyloxy]decyloxy)propane.
- 1,2,3-tris(10-[4-cyano-4'-biphenylacryloyloxy]decyloxy)propane.
- 1,2,3-tris(10-[4-methoxy-4'-biphenylacryloyloxy]decyloxy)propane.
- 1,2,3-tris(10-[4-ethoxy-4'-biphenylacryloyloxy]decyloxy)propane.
- 1,2,3-tris(10-[4-propyloxy-4'-biphenylacryloyloxy]decyloxy)propane.
- 1,2,3-tris(10-[4-butyloxy4'-biphenylacryloyloxy]decyloxy)propane.
- 1,2,3-tris(10-[4-pentyloxy-4'-biphenylacryloyloxy]decyloxy)propane.
- 1,2,3-tris(10-[4-hexyoxy-4'-biphenylacryloyloxy]decyloxy)propane.
- 1,2,3-tris(10-[4-heptoxy-4'-biphenylacryloyloxy]decyloxy)propane.
- 1,2,3-tris(10-[4-octyloxy-4'-biphenylacryloyloxy]decyloxy)propane.
- 1,2,3-tris(10-[4-(trans-4-pentylcyclohexyl)phenylacryloyloxy]decyloxy)propane.
- 1,2,3-tris(10-[anthracene-2-carbonyioxy]decyloxy)propane.
- 1,2,3-tris(10-[anthracene-9-carbonyloxy]decyloxy)propane.

EXAMPLE 9

Preparation of Aligned Twisted and Planar Nematic Cells

A 10 w/w % solution of 1,2,3-tris[5-(4-[(E)-ethoxycarbonylethenyl]phenoxy)pentanoyloxy]propane in cyclopentanone was spin coated at 2000 rpm for 30 seconds onto a fused silica substrate with indium tin oxide glass slides (24×25 mm$^2$). The coated substrates were dried at 80° C. for 30 min and then illuminated with linearly polarised ultra-violet light at 300.5 nm from an argon ion laser using the set-up shown in FIG. 3. The film anisotropy against UV exposure time was measured by determining the induced birefringence using a He—Ne laser at 632.8 nm. Twisted and planar nematic cells were prepared by combining the photoaligned substrate with a unidirectionally rubbed polyimide substrate whose orientation direction was either par- allel or orthogonal to that of the photoaligned substrate. An uniform cell gap was obtained by using mylar spacers (13 μm). The cells were filled with a nematic mixture (Merck E202) at 89° C. under vacuum by capillary action. On cooling either a twisted nematic or a planar cell was observed depending on how the substrates were combined. A twist angle of ≈90° was found for a twisted nematic cell using this cross-linked material exposed for 8 min at 15 mW.

An improvement in the performance of large, complex, nematic LCDs occurred in 1982 when it was observed that the voltage dependence of the transmission of nematic LC layers with twist angles in the range 180° to 270° could become infinitely steep, see C. M. Waters, V. Brimmell and E. P. Raynes, Proc. 3rd Int. Display Res. Conf., Kobe, Japan, 1983, 396. The larger twist angles are produced by a combination of surface alignment and making the nematic mixture into a long pitch cholesteric by the addition of a small amount of a chiral twisting agent. The increasing twist angle steepens the transmission/voltage curve, until it becomes bistable for 270° twist; for a specific twist angle between 225° and 270° the curve becomes infinitely steep and well suited to multiplexing. The larger twist angles present have resulted in the name supertwisted nematic (STN) for these LCDs.

Liquid Crystal Devices describing the use of STNs may be found in patent application GB 8218821 and resulting granted patents including U.S. Pat. No. 4,596,446. The alignment layers of the current invention may be included in many of the known devices including STNs. Other suitable types of display in which the current invention may be used include those that utilise the Dynamic Scattering Effect, the nematic guest host effect, cholesteric-nematic phase change effect, Electrically Controlled Birefringence, In-plane switching, Bistable nematics, Twisted Nematics. There are a number of different but related configurations of STN-LCDs in which the current invention may be used—these include the bistable 360° cholesteric effect—Berreman and Heffner, Journal of Applied Physics, 1981, 52, 3032, the bistable guest-host effect—Waters, Raynes and Brimmel, Molecular Crystals and Liquid Crystals, 1985, 123, 303, the superbirefringence effect—Scheffer and Nehring, Applied Physics Letters, 1984, 45, 1021, the double layer STN-LCD—Katoh et al, Japanese Journal of Applied Physics, 1987, 26, L1784 and Watanabe et al—Society for Information Displays, 1988, 416. The materials of the current invention may also be used in LCDs with an actively addressed matrix e.g. thin film transistors (TFT-LCDs).

What is claimed is:

1. A compound of Formula I:

Formula I wherein
$X_{1-5}$ are independently selected from H, F, CN, phenylene, and $C_{1-10}$ alkyl whereby when $X_1=X_2$, then $X_{1,2}=H$ and when $X_3=X_4$, then $X_{3,4}=H$
$S_{1-3}$ are independently selected from:
  an alkylene unit with 1 to 16 carbon atoms wherein one or more non-adjacent $CH_2$ groups are optionally substituted with COO, OOC or O;

a cycloalkylene group with 3 to 8 carbon atoms in which optionally one or two methylene units are replaced by NH groups;
phenylene, which is unsubstituted or is substituted from one and up to and including all available substitution positions with $C_{1-10}$ alkyl, $C_{1-10}$ alkoxy, CN, $NO_2$, halogen, or carbonate;

COO, OOC;
—CONH— and —NHOC—, the H group on the amide is optionally substituted with $C_{1-10}$ alkyl groups;
—C—O—C—; or
oxycarbonylphenoxyalkanoyloxy;
$PG_{1-3}$ are photoisomerisable/dimerisable groups selected from the following general formulae:

II wherein
A is 1,2-, 1,3- or 1,4-phenylene, which is unsubstituted or substituted from one and up to and including all available substitution positions with one or more of the groups selected from halogen, CN, $NO_2$ and in which optionally 1 or 2 CH groups are replaced by nitrogen, or A is 2,5-thiophenediyl, 2,5-furanylene, 1,4- or 2,6-naphthalene in which optionally 1 or 2 CH groups are replaced by nitrogen; or A is COO— in which case $S_{1-3}$ shall not have a terminal —O—;
$A_1$ is 1,2-, 1,3- or 1,4-phenylene, which is unsubstituted or substituted from one and up to and including all available substitution positions with one or more of the groups selected from halogen, CN or $NO_2$ and in which optionally 1 or 2 CH groups are replaced by nitrogen, or $A_1$ is pyrimidine-2,5-diyl, pyridine-2,5-diyl, 2,5-thiophenediyl, 2,5-furanylene, 1,4- or 2,6-naphthalene in which optionally 1 or 2 CH groups are replaced by nitrogen;
$A_{2,3}$ are each independently selected from 1,2-, 1,3- or 1,4-phenylene, which is unsubstituted or substituted from one and up to and including all available substitution positions with one or more of the groups selected from halogen, CN or $NO_2$ and in which optionally 1 or 2 CH groups are replaced by nitrogen;
or $A_{2,3}$ are each independently selected from pyrimidine-2,5-diyl, pyridine-2,5-diyl, 2,5-thiophenediyl, 2,5-furanylene, 1,4- or 2,6-naphthalene in which optionally 1 or 2 CH groups are replaced by nitrogen, trans-1,3-dioxane-2,5-diyl or 1,4-piperidyl;
$Z_{1,2}$ are each independently selected from a direct bond, $CH_2CH_2$, COO, OOC, $O(CH_2)_3$, $OCH_2$, $CH_2O$, $(CH_2)_3O$, or $(CH_2)_4$, or the trans form of $OCH_2CH=CH$, $CH_2CH=CHO$, $CH_2CH_2CH=CH$, or $CH_2CH=CHCH_2$;
$n_{1,2}$ are each independently 0 or 1;
W, Y are each independently selected from H, halogen, CN, alkyl with 1 to 12 carbon atoms which is optionally substituted with one or more fluorines and in which optionally 1 or 2 non-adjacent methylene units (CH$_2$) are replaced by oxygen, COO, OOC, CO and/or CH=CH;

R$_1$ is H, halogen, CN, NO$_2$, NCS, or alkyl with 1 to 12 carbon atoms which is optionally substituted with one or more fluorines and in which optionally 1 or 2 non-adjacent methylene units (CH$_2$) are replaced by oxygen, COO, OOC, CO and/or CH=CH;

or

III wherein

A$_{4,5}$ are each independently be selected from 1,2-, 1,3- or 1,4-phenylene, which is unsubstituted or substituted from one and up to and including all available substitution positions with one or more of the groups selected from halogen, CN or NO$_2$ and in which 1 or 2 CH groups are optionally replaced by nitrogen;

or A$_{4,5}$ are independently selected from pyrimidine-2,5-diyl, pyridine-2,5-diyl, 2,5-thiophenediyl, 2,5-furanylene, 1,4- or 2,6-naphthalene in which optionally 1 or 2 CH groups are replaced by nitrogen;

Z$_{3,4}$ are each independently selected from a direct bond, CH$_2$CH$_2$, COO, OOC, O(CH$_2$)$_3$, OCH$_2$, CH$_2$O, (CH$_2$)$_3$O, (CH$_2$)4, or the trans form of OCH$_2$CH=CH, CH$_2$CH=CHO, CH$_2$CH$_2$CH=CH or CH$_2$CH=CHCH$_2$;

n$_{3,4}$ are each independently 0 or 1;

A$_6$ is

A$_7$ are 1,2-, 1,3- or 1,4-phenylene, which is unsubstituted or substituted from one and up to and including all available substitution positions with one or more of the groups selected from halogen, CN or NO$_2$ and in which optionally 1 or 2 CH groups are replaced by nitrogen, or A$_7$ is 2,5-thiophenediyl, 2,5-furanylene, 1,4- or 2,6-naphthalene in which optionally 1 or 2 CH groups are replaced by-nitrogen, trans-1,3-dioxane-2,5-diyl or 1,4-piperidyl Z$_5$ is an alkylene unit with 1 to 16 carbon atoms, a cycloalkylene group with 3 to 8 carbon atoms in which optionally one or two methylene units are replaced by NH groups, or phenylene, which can be substituted with C$_{1-10}$ alkyl, C$_{1-10}$ alkoxy, CN, NO$_2$, halogen, or carbonate, COO and OOC;

—CONH— and —NHOC—, the H group on the amide may be substituted with C$_{1-10}$ alkyl groups;

—C—O—C—;

n$_5$ is 0 or 1;

R$_2$ is H, halogen, CN, NO$_2$, NCS, SCN or alkyl with 1 to 12 carbon atoms which is optionally substituted with one or more fluorines and in which optionally 1 or 2 non-adjacent methylene units (CH$_2$) are replaced by oxygen, COO, OOC, CO and/or CH=CH;

R$_3$ is H, halogen, CN, NO$_2$, NCS, SCN or alkyl with 1 to 12 carbon atoms which is optionally substituted with one or more fluorines and in which optionally 1 or 2 non-adjacent methylene units (CH$_2$) are replaced by oxygen, COO, OOC, CO and/or CH=CH;

R$_4$ is H or C$_{1-10}$ alkyl;

V is H, alkyl or alkoxy with 1 to 8 carbon atoms, trifluoromethyl, or phenyl which may be substituted from one and up to and including all available substitution positions with one or more of the groups selected from CN, halogen or NO$_2$;

U is H, alkyl or alkoxy with 1 to 8 carbon atoms, cyano, or COOR$_5$;

R$_5$ is C$_{1-10}$ alkyl;

r is a number from 0 to 3;

X$_{6,7}$ is independently selected from H, halogen, CN, NO$_2$, NCS, SCN or alkyl with 1 to 12 carbon atoms which is optionally substituted with one or more fluorines and in which optionally 1 or 2 non-adjacent methylene units (CH$_2$) are replaced by oxygen, COO, OOC, CO and/or CH=CH.

2. A compound according to claim 1, wherein PG$_{1-3}$ have the general formula IIIA

IIIA wherein
  $A_4$ may be 1,4-phenylene, which is unsubstituted or substituted from one and up to and including all available substitution positions with one or more of the groups selected from the halogen, CN or $NO_2$.

3. A compound according to claim 1, wherein the photoisomerisable/dimerisable groups $PG_{1-3}$ have the formula:

IIA wherein
  $S_1$ indicates the position of a spacer group
  $A_1$ is 1,4-phenylene, which is unsubstituted or substituted from one and up to and including all available substitution positions with one or more of the groups selected from halogen, CN, $NO_2$;
  or pyrimidine-2,5-diyl, pyridine-2,5-diyl, 2,5-thiophenediyl, 2,5-furanylene, 1,4- or 2,6-naphthalene;
  $A_2$ is 1,4-phenylene, which is unsubstituted or substituted from one and up to and including all available substitution positions with one or more of the groups selected from halogen, CN, $NO_2$;
  or pyrimidine-2,5-diyl, pyridine-2,5-diyl, 2,5-thiophenediyl, 2,5-furanylene, trans-1,3-dioxane-2,5-diyl or 1,4-piperidyl;
  $Z_1$ is a direct bond, $CH_2CH_2$, COO, OOC, $O(CH_2)_3$, $OCH_2$, $CH_2O$, $(CH_2)_3O$, or $(CH_2)_4$;
  $n_1$ is 0 or 1;
  W, Y are each independently H, halogen, CN, alkyl with 1 to 12 carbon atoms which is optionally substituted with one or more fluorines;
  $R_1$ is H, halogen, CN, alkyl with 1 to 12 carbon atoms which is optionally substituted with one or more fluorines and in which optionally 1 or 2 non-adjacent methylene units ($CH_2$) are replaced by oxygen, COO, OOC and/or CH=CH.

4. A compound according to claim 1 wherein the photoisomerisable/dimerisable groups $PG_{1-3}$ have the formula:

IIIA wherein
  $A_4$ is 1,4-phenylene, which is unsubstituted or substituted from one and up to and including all available substitution positions with one or more of the groups selected from halogen, CN and $NO_2$;
  or is pyrimidine-2,5-diyl, pyridine-2,5-diyl, 2,5-thiophenediyl, 2,5-furanylene, 1,4- or 2,6-naphthalene;
  $Z_3$ is a direct bond, $CH_2CH_2$, COO, OOC, $O(CH_2)3$, $OCH_2$, $CH_2O$, $(CH_2)_3O$, or $(CH_2)_4$;
  $n_3$ is 0 or 1;
  $A_6$ is $R_2$ is alkyl with 1 to 12 carbon atoms which is optionally substituted with one or more fluorines and in which optionally 1 or 2 non-adjacent methylene units ($CH_2$) are replaced by oxygen, COO, OOC and/or CH=CH.

5. A compound according to claim 1, wherein $S_{1-3}$ are independently selected from oxycarbonylalkanoyloxy, oxyalkoxy, oxycarbonylalkoxy, oxyalkanoyloxy, oxycarbonylphenoxyalkanoyloxy, and oxyalkoxyalkyl containing from 1–16 carbon atoms.

6. A compound according to claim 1 wherein halogen is chlorine or fluorine.

7. A method of providing an alignment layer on a surface of a liquid crystal cell wall comprising the steps of:
  (a) depositing a layer of material comprising at least one compound according to claim 1 on the surface; and thereafter
  (b) exposing the material to actinic radiation.

8. A method according to claim 7 wherein the radiation is in the range of 250–450 nm.

9. A liquid crystal device comprising a layer of liquid crystal material between two cell walls, the cell walls both carrying electrode structures and surface treated to provide an alignment layer for liquid crystal molecules; wherein the surface treatment is a layer of material comprising a compound according to claim 1 which has been exposed to actinic radiation.

10. A liquid crystal device according to claim 9 wherein the device is an Active Matrix Device.

11. A liquid crystal device according to claim 9 wherein the device is an STN device.

12. A device according to claim 9 wherein the radiation is in the range 250–450 nm.

* * * * *